United States Patent [19]

Gannon

[11] Patent Number: 4,724,837
[45] Date of Patent: Feb. 16, 1988

[54] METHOD AND APPARATUS FOR PERFORMING RADIAL KERATOTOMY REFRACTIVE EYE SURGERY

[76] Inventor: Marc J. Gannon, 20827 Sonrisa Way, Boca Raton, Fla. 33433

[21] Appl. No.: 804,818

[22] Filed: Dec. 4, 1985

[51] Int. Cl.[4] .............................................. A61F 17/32
[52] U.S. Cl. ...................................... 128/305; 30/321
[58] Field of Search ................ 128/305, 305.3, 303 R, 128/751–754, 253, 302, 315; 30/315, 294, 321, 320

[56] References Cited

U.S. PATENT DOCUMENTS

| | | |
|---|---|---|
| 3,074,407 | 1/1963 | Moon et al. . |
| 3,502,070 | 3/1970 | Bliss . |
| 3,945,117 | 3/1976 | Beaver . |
| 4,192,312 | 3/1980 | Wilson . |
| 4,205,682 | 6/1980 | Crock et al. . |
| 4,340,059 | 7/1982 | Marinoff . |
| 4,406,285 | 9/1983 | Villasewor et al. . |
| 4,417,579 | 11/1983 | Soloviev et al. . |
| 4,520,815 | 6/1985 | Marinoff . |
| 4,619,259 | 10/1986 | Graybill et al. ...................... 128/305 |

Primary Examiner—Henry A. Bennet
Attorney, Agent, or Firm—Renner, Otto, Boisselle & Lyon

[57] ABSTRACT

An apparatus and a method for performing radial keratotomy refractive eye surgery. A plurality of blades are supported in predetermined relation to the cornea of a patient's eye. The blades are simultaneously moved along predetermined paths to simultaneously make radial incisions in the cornea. The blade paths are carefully and precisely controlled, so that the cutting depth and the length of the radial incisions can be precisely made.

15 Claims, 8 Drawing Figures

METHOD AND APPARATUS FOR PERFORMING RADIAL KERATOTOMY REFRACTIVE EYE SURGERY

BACKGROUND OF THE INVENTION

This invention pertains generally to the art of radial keratotomy refractive eye surgery and in particular to a method and apparatus for making a plurality of radial incisions of predetermined length and depth simultaneously in the cornea of an eye.

Radial keratotomy is a surgical procedure for the correction of myopia or nearsightedness under which a series of radial incisions are made into the cornea of the eye. These incisions cause the peripheral portion of the cornea to bulge outward and, cause the central portion of the cornea to flatten, thus correcting the patient's vision.

The thickness, curvature and size of the cornea along with the degree of the nearsightedness and age and sex of the patient determine (i) the number of incisions to be made, (ii) the depth of the incisions, (iii) the length of the incisions and (iv) the size of the optical zone, i.e., the uncut central portion of the cornea. The procedure usually takes about fifteen to twenty minutes and requires four to sixteen incisions.

Heretofore, it has been conventional to make individual incisions sequentially, and by hand. Because of the amount of time required and the number of incisions involved, there are many problems associated with such current procedures. One problem is keeping the incisions properly straight and evenly spaced. During surgery, the cornea swells (thickens) and softens (e.g., because of the trauma involved), making the last few incisions much more difficult than earlier ones.

Additionally, the cornea is much thicker at the periphery than at the central or optical zone. Frequently, second cuts in the original incisions are required near the periphery of the cornea to obtain the desired depth of incision.

Still further, during the surgery care must also be taken to ensure that the incisions are not too long or too deep. The incisions should not be so long so as to extend into the sclera, the white part of the eye. The incisions also should not be so deep so as to extend through descemets membrane of the eye.

Moreover, when surgical incisions have to be made sequentially, by hand, there is always an attendant risk of non-uniformity or non-precision of incision, and this risk is magnified by the risk of softening of the cornea described above.

Others have tried various means to obviate some of these complications. For example, Villasenor, et al., U.S. Pat. No. 4,406,285, disclose a semispherical template with radial slots to ensure straight, evenly spaced incisions. Cutting depth is limited by varying the thickness of the template. However, a surgeon must still make each incision manually. Thus, the last incisions are still more difficult to make than earlier ones because the cornea will begin to thicken as additional cuts are made.

SUMMARY OF THE INVENTION

The present invention provides an instrument and a method designed to overcome the types of problems described above. The present invention, in one of its most significant aspects, provides an apparatus and a method by which a plurality of radial incisions are simultaneously made in the cornea. This concept dramatically reduces the time of a surgical procedure. Also, it eliminates the problems attendant with the type of softening of the cornea which occurs when incisions are made sequentially. Moreover, it enables the cornea to be cut in one pass of the surgical blades, even though the cornea has a different thickness toward its outer periphery. Still further, it minimizes the risk of non-uniformity or non-precision of incision that is attendant with the making of incisions sequentially, by hand.

According to the invention, a plurality of surgical blades are supported in predetermined relation to the cornea of a patient's eye. The blades are then simultaneously moved along predetermined paths to simultaneously make radial incisions in the cornea. This eliminates the problem of the last cuts being more difficult than the earlier cuts. The blade paths are carefully and precisely controlled, so that the cutting depth at the periphery of the cornea can be varied. This eliminates the need for second cuts at the periphery. The apparatus of the invention includes actuation means for simultaneously activating the blades, along precisely controlled paths, to ensure consistent and precise incisions.

The preferred embodiment of the invention also includes adjustment means for precisely predetermining the length and depth of the incisions during the procedure. Thus, the incisions can be precisely controlled, and can be maintained within predetermined length and depth limits.

Therefore, with the foregoing in mind, it is an object of the invention to overcome the imprecisions of manual radial keratotomy and to provide an apparatus and method which helps surgeons to operate simply and with precision.

Another object of the invention is to provide an apparatus for performing radial keratotomy with which a surgeon need only actuate the cutting blades via an actuator, thus eliminating errors common in manual surgery.

Still another object of the invention is to enable precisely controlled incisions to be simultaneously made in the cornea of an eye.

These and other objects, features and advantages of the invention will be more fully understood and appreciated upon reference to the following detailed description taken in conjunction with the drawings wherein:

DETAILED DESCRIPTION OF THE PREFERRED EMBODIMENT

The apparatus of the present invention comprises an instrument 10 carrying a plurality of surgical blades 12. The blades are made of material (e.g. surgical steel, diamond) which is biocompatible and which is capable of making precise incisions in the cornea of an eye. The instrument 10 is designed to support the surgical blades 12 in a manner which enables the blades 12 to be precisely located relative to the cornea of a patient's eye. Further, the instrument is designed to simultaneously move the blades 12 along predetermined, precisely controlled paths in order to simultaneously form incisions in the patient's cornea.

Figure 1:
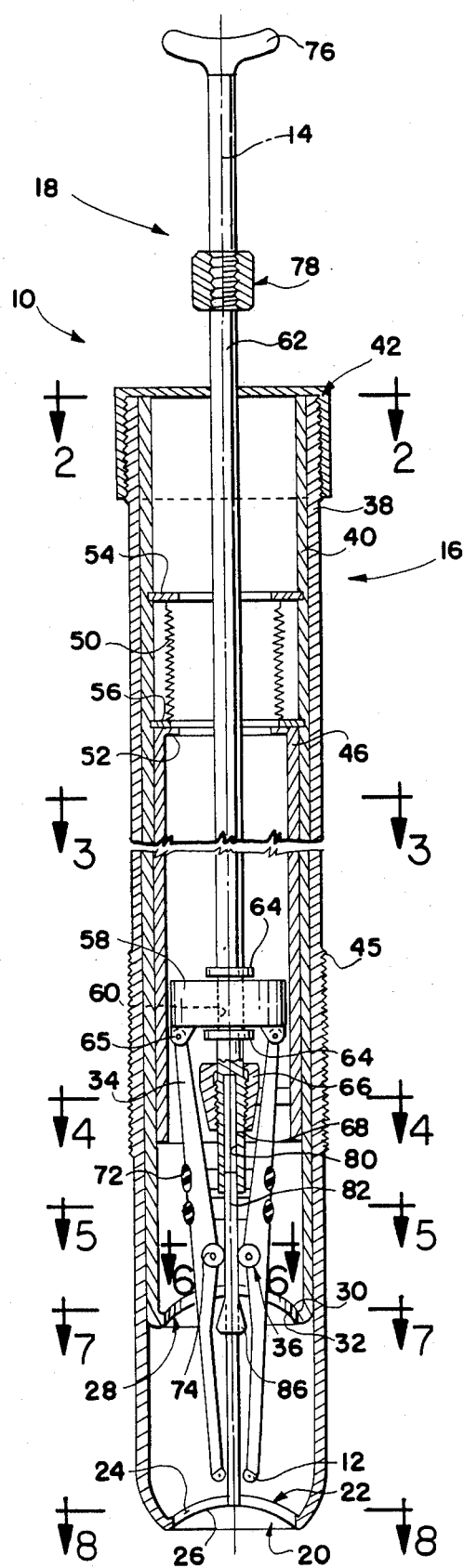
FIG. 1 is a cross sectional view of the apparatus according to the invention.

As seen in FIG. 1, the instrument 10 extends longitudinally relative to a central axis 14. The geometry of a patient's cornea would extend both radially and longitudinally relative to the longitudinal central axis 14, and the blades 12 are moved along paths which makes incisions in the patient's cornea that have both a radial and longitudinal extent. In this application, references to radial incisions, directions or paths refers to incisions, directions or paths which extend radially in relation to the longitudinal central axis 14 of the instrument and which may have a depth that extends axially in relation to the longitudinal axis 14 of the instrument 10.

Also, in this application, reference to an "arcuate" surface is intended to encompass a three dimensional surface which has a curved profile when viewed in a plane that includes the longitudinal central axis 14. Moreover, the term "arcuate" is intended to be broad enough to encompass a curved surface which is complex in origin, in the sense that it does not have to originate from a single fixed point.

The instrument 10 includes a housing 16 enclosing the plurality of blades 12, an actuator 18 extending outwardly from one end of the housing 16, and a corneal shield 20 at the other end of the housing 16.

Figure 8:
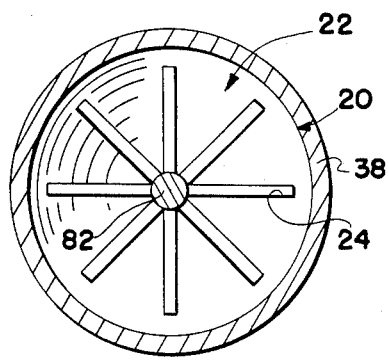
FIG. 8 is a cross sectional view of the apparatus of FIG. 1, taken along the line 8—8.

The corneal shield 20 engages the cornea of a patient's eye, and locates the instrument 10 relative to the cornea. The corneal shield 20 comprises an arcuate member 22 with a plurality of radial slots 24 (FIG. 8), and an arcuate outer surface 26. The corneal shield 20 is removably supported in the housing 16, so that different corneal shields, with different geometrical properties may be supported on the instrument 10. For example, different corneal shields could have different numbers of radial slots 24 and/or different arcuate profiles, in order to vary the number of incisions and/or to match different arcuate profiles of different patients' cornea.

An upper guide cam 28 is located in the housing 16, and is spaced from the corneal shield 20. Upper guide cam 28 has an arcuate geometry and an upper cam surface 30. Upper guide cam 28 also has a plurality of radial slots 32 extending therethrough. The radial slots 32 in the upper guide cam 28 are equal in number to the number of radial slots 24 in the corneal shield 20, and each radial slot 32 in the upper guide cam 28 is axially aligned with a respective radial slot 24 in the corneal shield 20. However, the profile of the upper guide cam 28 is not necessarily identical to the profile of the corneal shield 20. More specifically, the axial thickness of the guide cam 28 may vary relative to the axial thickness of the corneal shield 20, as those members extend radially away from the axis 14. Also, the arcuate profile of the cam surface 30 of the guide cam 28 can vary relative to either of the arcuate surface(s) of the corneal shield 20.

The surgical blades 12 are mounted on supporting arms 34 that extend through the radial slots 32 in the guide cam 28. The supporting arms are also dimensioned so that they can also extend at least partially through the radial slots 24 in the corneal shield 20. The radial slots 32, 24 in the guide cam 28 and the corneal shield 20 are precisely dimensioned to guide the blades along predetermined radial paths. The arcuate cam surface 30 of the guide cam 28 is designed to be engaged by cam followers 36 on the blade arms 34 to also control the geometrical path of the blades 12 as they are being moved radially, as explained more fully hereinafter.

The difference in the profile of the upper guide cam 28 relative to the profile of the corneal shield is most pronounced toward the radial extremities of those elements. For example, the axial thickness of those elements may be varied toward the radial extremities of the elements. Also, the arcuate profile of cam surface 30 may be more curved toward its radial extremity than the arcuate profile of either of the arcuate surfaces of the corneal shield 20. This enables the cutting depth of the blades 12 to be varied as the blades 12 are moved radially outwardly from the axis 14.

Figure 2:
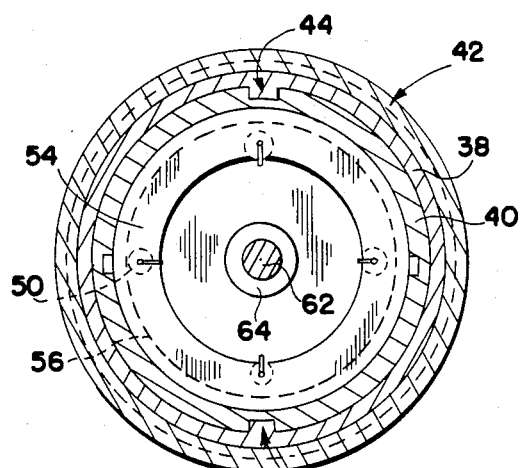
FIG. 2 is a cross sectional view of the apparatus of FIG. 1, taken along the line 2—2.
Figure 3:
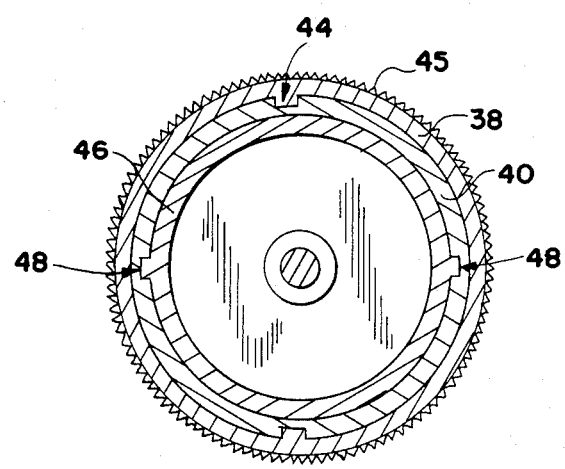
FIG. 3 is a cross sectional view of the apparatus of FIG. 1, taken along the line 3—3.

The housing 16 preferably comprises an outer casing 38 and an inner casing 40. Both casings are made of metal or plastic and are of hollow tubular (preferably circular) construction. The inner casing 40, however, is of smaller diameter and shorter length than outer casing 38. At the upper end of the instrument 10, a rotatable micrometer member 42 has a threaded engagement with the outer casing 38. The rotatable micrometer member 42 can be rotated to cause outer casing 38 to be moved axially relative to inner casing 40. Inner casing 40 is inhibited fro rotating relative to outer casing 38 by key and slot connections 44 between those members (see FIGS. 2 and 3).

The outer casing 38 has a knurled surface portion 45 to enable the instrument to be securely held by a surgeon. Also, the lower edge of outer casing 38 is bent slightly inwardly. Removably attached thereto is the corneal shield 20. The corneal shield 20 is preferably attached to the outer casing 38 by a snap-in connection (not shown). The corneal shield 20 is attached such that its concave outer surface 26 faces downward. Upper guide cam 28 is attached on the lower end of inner casing 40. Upper guide cam 28 is oriented such that its upper convex cam surface 30 faces away from the corneal shield 20.

When the inner casing 40 is caused to move axially relative to outer casing 38, upper guide cam 28 is caused to move axially relative to corneal shield 20. Thus, the relative distance between the upper guide cam 28 and the corneal shield 20 is selectively variable. Such adjustment enables the cutting (incision) depth of blades 12 to be varied because the extent to which the blades 12 will extend beyond the corneal shield 20 varies as a function of the distance between the corneal shield 20 and the upper guide cam 28.

A blade carriage 46 is disposed within inner casing 40. The blade carriage 46 is also of general hollow tubular construction. The blade carriage 46 is free to slide axially relative to the inner casing 40 but is inhibited from rotating relatively thereto by key and slot connections 48 (see FIG. 4). The blade carriage 46 is also attached to inner casing 40 via retractor springs 50 which are attached to rims 52 on the upper edge of the blade carriage 46, and to rims 54 fixed to the inner casing 40. The retractor springs 50 bias the blade carriage 46 in an upward direction. Upward movement of the blade carriage 46 is limited by retractor stops 56 secured to the inner walls of the inner casing 40.

The blade carriage 46 includes an annular horizontally extending platform 58 with an opening 60 dimensioned to allow relative axial movement of a central plunger 62 forming part of the actuator 18. The blade carriage 46 is inhibited from moving axially relative to the plunger 62 by more than predetermined amounts by a pair of O-rings 64 located on either side of the platform 58. However, the central plunger 62 is free to rotate in the opening 60 formed in the platform 58 in blade carriage 46.

The upper ends of the blade support arms 34 are hingedly attached to the bottom of the platform 58 on the blade carriage 46. Specifically, each blade support 54 is hinged to an axle connected to a respective pair of support members 65 on the platform 58. Thus, the blade support arms 34 can move up and down with the platform 58, and can pivot about their respective axles as they move radially. However, the axles restrain the blade support arms against twisting.

Figure 4:
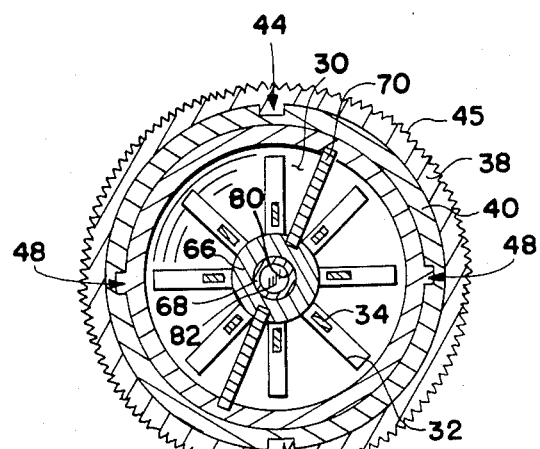
FIG. 4 is a cross sectional view of the apparatus of FIG. 1, taken along the line 4—4.
Figure 5:
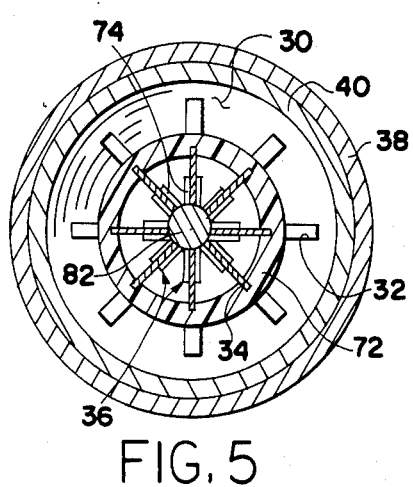
FIG. 5 is a cross sectional view of the apparatus of FIG. 1, taken along the line 5—5.
Figure 6:
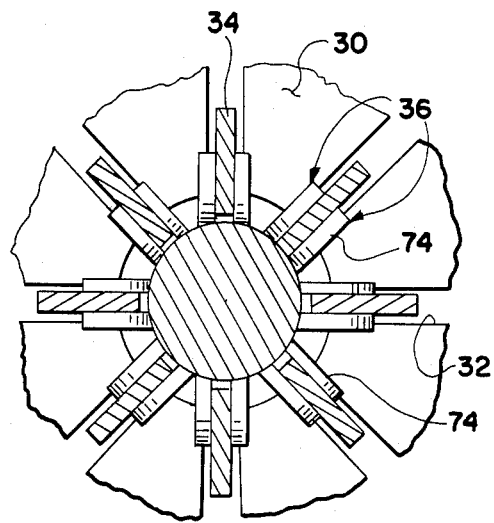
FIG. 6 is a cross sectional view of the apparatus of FIG. 1, on an enlarged scale, taken along the line 6—6.
Figure 7:
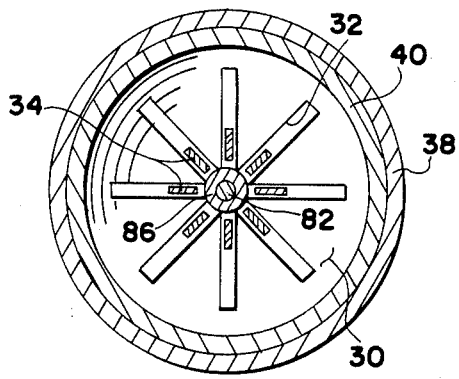
FIG. 7 is a cross sectional view of the apparatus of FIG. 1, taken along the line 7—7.

The blade support arms 34 are separated by wedge 66 disposed therebetween. The wedge 66 has a threaded inner profile that engages a threaded portion 68 of the central plunger 66. The wedge 66 is inhibited from rotating by arms 70 which have key and slot connections with the wedge 66 and the blade carriage 46 (FIG. 4). Thus rotating central plunger 62 causes the wedge 66 to move axially along the plunger 62 in order to adjust the separation between the blade arms 34.

The blade support arms 34 are tensioned radially inward by coil retaining springs 72. When the wedge 66 is moved upwardly or downwardly, the blade support arms 34 move radially inwardly or apart respectively, as described more fully hereinafter. This allows a precise setting of the radial separation of the blade support arms 34 upon initial corneal contact. Thus, the optical zone setting the radially inward portion of the cornea left uncut, can be precisely predetermined.

The blade support arms 34 have the cam followers 36 thereon. The cam followers 36 preferably comprise pairs of roller bearing members 74 pivotably secured to respective blade support arms 34. The roller bearing members 74 are normally disposed above cam surface 30, and are adapted to move downwardly by operation of the actuator 18. When they move downwardly, the roller bearing members 74 engage cam surface 30 and then follow its arcuate profile. The blade support arms 34 can pivot about the support members 65 and can pivot about the roller bearings 74 as the roller bearings 74 follow the cam profile.

The central plunger 62 has an actuator handle portion 76 is disposed outwardly of the housing. The actuator handle portion 76 carries a length limiting micrometer 78. The incision length limiting micrometer 78 has a inner surface threadingly engaged to the plunger 62, and by rotating the micrometer 78, the micrometer 78 is caused to move axially along the plunger. The micrometer 78 functions to adjust the length of stroke of the actuator 18, to adjust the incision length, as further explained below. The micrometer 78 does not impede the plunger 62 from rotating, to adjust the optical zone setting.

The portion 68 of the central plunger 62 has an axial bore 80 which receives the upper end of a guide rod 82 therein. When the central plunger 68 is moved downward it moves the blade carriage 46 downward. When the blade carriage 46 moves downward the platform 58 exerts downward pressure on the blade support arms 34. The lower end 68 of the central plunger 62 slides on the guide rod 82. The spring bias on roller bearings 74 causes them to also bear on the guide rod 82, until they engage cam surface 30 and are urged along its arcuate profile. The guide rod 82 ensures stablity of the central plunger 62 thus ensuring stability of the instrument during incisions. Integral with the guide rod 82 is a fixed separation wedge 86 which further ensures a minimum separation of the blade supporting arms 34 and which can help initiate radial movement of the blade support arms during an incision.

In performing radial keratotomy refractive eye surgery, a surgeon first marks the cornea, preferably with a separate instrument, to provide a reference point on the cornea. The surgeon then presets the incision length, optical zone and incision dept by setting the incision depth limiting micrometer 42, the incision length limiting micrometer 78, and the initial separation of the blade support arms 34 set by the wedge 66. Once these settings are made, the instrument is then placed on the cornea with the corneal shield 20 located centrally on the cornea in predetermined relation to the marked reference point. The surgeon then actuates the blades by depressing the actuator 18 to move the plunger 62 downward. As the plunger 62 moves downward, the blade carriage 46 moves downward and exerts downward pressure on the blade support arms 34. The blade support arms 34 and the blades 12 are moved downwardly through the radial slots 24 in the corneal shield 20 and make their initial penetration into the cornea at a radial location determined by the optical zone setting. The amount by which the blades can initially penetrate the cornea depends at least in part upon the axial distance the roller bearings 36 move through before they make initial contact with the cam surface 30 of the upper guide cam 28.

As the plunger 62 is depressed further, the blade support arms 34 can pivot in the support members 65 and on the roller bearings 36. The blade support arms 34 and the blades 12 move along radial paths defined by the radial slots 34, 24 in the cam guide 28 and the corneal shield 20, and simultaneously make radial incisions in the cornea. The blades 12 continue their radial length of travel until the incision length limiting micrometer 78 makes contact with the top of the incision depth micrometer 42. The plunger 62 at this point is inhibited from further depression; thus the blades 12 cannot be forced to travel further and the incisions are complete. Upon release of the actuator 18, the retractor springs 50 and the springs 72 cooperate to bias the elements to their original positions.

The foregoing structure allows precise control over the paths of the incisions. The relative actuate profiles of the corneal shield 20 and the cam surface 30, the relative thicknesses of the corneal shield 20 and cam guide 28, and the number of radial slots can all be precisely dimensioned to control the basic blade paths. The various micrometer settings can be used to provide extremely fine adjustment of blade length and depth profiles, to precisely control the length and depth of the incisions. For example, the profiles of the corneal shield and cam surface can be selected, and the various micrometer settings adjusted, so that the blade cutting depth profile increases as the blades are moved radially outward, thus enabling a single incision to accurately cut a thin incision at the radially inner part of the cornea, and a deeper incision toward the periphery of the cornea.

While the preferred embodiment of the invention has been disclosed, it will be understood that various modifications obvious to one skilled in the art can be made thereto without departing from the spirit and scope of the invention as covered in the appended claims.

What is claimed:

1. Apparatus for performing radial keratotomy refractive eye surgery comprising means for supporting a plurality of surgical blades, means for locating the plurality of surgical blades in predetermined relation to the cornea of an eye; and means for simultaneously moving the blades along predetermined radial paths to simultaneously make a plurality of incisions in the cornea; said means for supporting the plurality of surgical blades comprising a housing; said means for locating the plurality of surgical blades in predetermined relation to the cornea of an eye comprising a corneal shield having an arcuate surface for engaging the cornea of an eye and for locating the housing in predetermined relation to the cornea of the eye; said means for simultaneously moving the plurality of surgical blades along predetermined radial paths comprising guide means having a series of radial slots for guiding respective blades in predetermined radial directions, said guide means comprising a cam surface with an arcuate profile; said means for simultaneously moving the blades further a series of cam followers connected with respective blades and designed to engage the cam surface, and means for simultaneously moving the cam followers radially along the arcuate profile of the cam surface to move the blades radially in their respective radial slots.

2. Apparatus as set forth in claim 1 wherein the corneal shield and the cam surface have arcuate profiles that vary in relation to each other as they extend radially, in order to vary the depth of cut of the blades as they move radially relative to the corneal shield.

3. Apparatus a set forth in claim 2 further including means for predetermining the cutting depth profiles of the blades as they are moved in their predetermined radial directions.

4. Apparatus as set forth in claim 3 including means for controlling the radial lengths of the incisions made by the blades as they move in their respective radial directions.

5. Apparatus as set forth in claim 4 including means for predetermining the initial location of the cut made by each of the blades.

6. Apparatus as set forth in claim 1 wherein said means for supporting said plurality of blades comprises a housing, a blade carriage axially movable in said housing, a plurality of blade support arms connected with said blades and with said blade carriage, each blade support arm being axially movable with said blade carriage and being radially movable relative to said blade carriage, an axially movable actuator member extending into said housing and adapted to engage said blade carriage and to move said blade carriage axially in said housing, said cam followers being connected with respective blade support arms, and said cam surface being adapted to engage said cam followers and to guide said blade support arms along their predetermined radial paths as said blade carriage is moved axially in said housing.

7. Apparatus as set forth in claim 6, wherein said corneal shield has a plurality of radially extending slots which extend axially therethrough and are adapted to guide respective surgical blades along predetermined radial paths, said blade carriage being biased away from said corneal shield and being movable toward said corneal shield by said actuator member, said blade support arms being adapted to simultaneously move said blades at least partially through their respective radially extending slots in the corneal shield when said blade carriage is moved toward said corneal shield to enable the blades to effect incisions of the cornea of an eye as the blade carriage is moved toward the corneal shield.

8. Apparatus as set forth in claim 7 including an arcuate cam guide spaced from said corneal shield, said arcuate cam guide comprising an arcuate surface defining said cam surface and a plurality of radially extending slots axially aligned with respective radially extending slots in the corneal shield, each blade support arm extending through a respective radially extending slot in said cam guide and being axially movable therein as said blade carriage is moved toward said corneal shield, each blade support arm being guided along a predetermined radial path by its respective radially extending slot in said cam guide as its associated cam follower is moved radially along said cam surface of said cam guide.

9. Apparatus as set forth in claim 8 including means for predetermining the extent to which each of the blades will extend through the corneal shield as the blades are moved axially and radially relative to the corneal shield to predetermine the depth profile of the incisions made by the blades.

10. Apparatus as set forth in claim 9 including means for predetermining the range of radial movement of the blades while the blades are extending through the corneal shield to predetermine the radial extent of the incisions made by the blades.

11. Apparatus for performing radial keratotomy refractive eye surgery, comprising a blade means for locating said blade in predetermined relation to the cornea of an eye, and actuator means for moving said blade along a predetermined radial path to make a surgical incision in the cornea;

said blade comprises a housing, a blade carriage axially movable in said housing, a blade support arm connected to said blade and to said blade carriage, said blade support arm being axially movable with said blade carriage and being radially movable relative to said blade carriage, an axially movable actuator member extending into said housing and adapted to engage said blade carriage and to move said blade carriage axially in said housing, cam follower means connected to said blade support arm, and a cam surface for engaging said cam follower means and for guiding said blade support arm along said predetermined radial path as said blade carriage is moved radially in said housing.

12. Apparatus as set forth in claim 11, wherein said means for locating said surgical blade comprises a corneal shield having an arcuate surface for engaging the cornea of an eye, said corneal shield having a radially extending slot extending axially therethrough and adapted to guide the surgical blade along said predetermined radial path, said blade carriage being biased away from said corneal shield and being movable toward said corneal shield by said actuator member, said blade support arm being dimensioned to move said blade at least partially through the radially extending slot in the corneal shield when said blade carriage is moved toward said corneal shield to enable the blade to effect an incision of the cornea of an eye as the blade carriage is moved toward the corneal shield.

13. Apparatus as set forth in claim 12 including an arcuate cam guide spaced from said corneal shield, said arcuate cam guide comprising an arcuate surface defining said cam surface and a radially extending slot axially aligned with the radially extending slot in the corneal shield, said blade support arm extending through the radially extending slot in said cam guide and being axially and radially movable therein as said blade carriage is moved toward said corneal shield, said blade support arm being guided along a predetermined radial path by said radially extending slot in said cam guide as said cam follower is moved radially along said cam surface of said cam guide.

14. Apparatus as set forth in claim 13 including means for predetermining the extent to which the blade will extend through the corneal shield as the blade is moved axially and radially relative to the corneal shield to predetermine the depth profile of the incision made by the blade.

15. Apparatus as set forth in claim 14 including means for predetermining the range of radial movement of the blade while the blade is extending through the corneal shield to predetermine the radial extent of an incision made by the blade.

* * * * *